United States Patent [19]

Nadelson

[11] 4,136,114
[45] Jan. 23, 1979

[54] 2-AMINOMETHYLENE-5-HYDROXY-N-ALKYL-3-OXO-AMIDES

[75] Inventor: Jeffrey Nadelson, Lake Parsippany, N.J.

[73] Assignee: Sandoz, Inc., E. Hanover, N.J.

[21] Appl. No.: 822,256

[22] Filed: Aug. 5, 1977

Related U.S. Application Data

[62] Division of Ser. No. 700,066, Jun. 25, 1976, Pat. No. 4,060,533.

[51] Int. Cl.$^2$ .............. C07C 103/133; C07C 103/22; C07C 103/28
[52] U.S. Cl. .......................... 260/559 A; 260/561 A; 260/562 B
[58] Field of Search .......... 260/559 D, 559 A, 561 A, 260/561 N, 561 B

[56] References Cited

U.S. PATENT DOCUMENTS

| | | |
|---|---|---|
| 2,851,494 | 9/1958 | Ehrhart et al. .............. 260/559 A X |
| 3,498,995 | 3/1970 | McGregor et al. ...... 260/559 A UX |
| 3,882,174 | 5/1975 | Seeger et al. ................ 260/559 A X |

*Primary Examiner*—Allen B. Curtis
*Attorney, Agent, or Firm*—Gerald D. Sharkin; Robert S. Honor; Timothy G. Rothwell

[57] ABSTRACT

2-Aminomethylene-5-hydroxy-N-alkyl-3-oxo-amides.

2 Claims, No Drawings

2-AMINOMETHYLENE-5-HYDROXY-N-ALKYL-3-OXO-AMIDES

This is a division of application Ser. No. 700,066 filed June 25, 1976, now U.S. Pat. No. 4,060,533.

This invention relates to 4-oxo-pyrancarboxamide derivatives. In particular, this invention relates to alkyl and aryl substituted 4-oxo-4H-pyran-3-carboxamides, processes, and intermediates used in their preparation and their use in pharmaceutical compositions.

The compounds of this invention may be represented by the following structural formula:

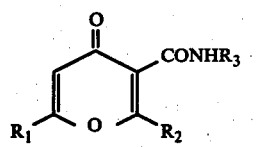

where $R_1$ and $R_2$ each independently is lower alkyl, i.e., alkyl having 1 to 4 carbon atoms, e.g., methyl, ethyl, isopropyl, and the like or

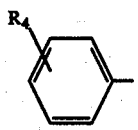

where $R_4$ is hydrogen, halogen having an atomic weight of from 19 to 36, lower alkoxy, i.e., alkoxy having 1 to 4 carbon atoms, e.g., methoxy, ethoxy, and the like or lower alkyl as defined above and is lower alkyl as defined above.

The compounds of formula (I) may be prepared in accordance with the following reaction scheme:

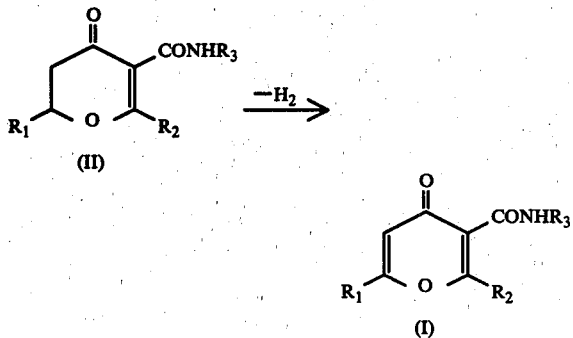

where $R_1$, $R_2$, and $R_3$ are as defined above.

The compounds of formula (I) are prepared by dehydrogenating a compound of the formula (II) in an inert solvent in the presence of a dehydrogenating agent. The dehydrogenating agent can be any of the standard dehydrogenating agents, such as sulfur or dichlorodicyanoquinone, the latter being especially preferred. Although the particular inert solvent employed is not critical, it is preferred that the reaction be carried out in an inert solvent such as the aromatic hydrocarbons, e.g., benzene, toluene, and the like, especially benzene, or halogenated hydrocarbons, e.g., ethylene dichloride, dichlorobenzene, and the like. The temperature at which the reaction is carried out is not critical, but it is preferred that the reaction be run between about 50° C. to 180° C., preferably between about 80° C. to 120° C. The time of the reaction also is not critical, but it is preferred that the reaction be run for 5 to 24 hours, especially 16 to 20 hours. The compounds of formula (I) are isolated by conventional techniques, e.g., extraction and evaporation.

The compounds of formula (II) may be prepared in accordance with the following reaction scheme:

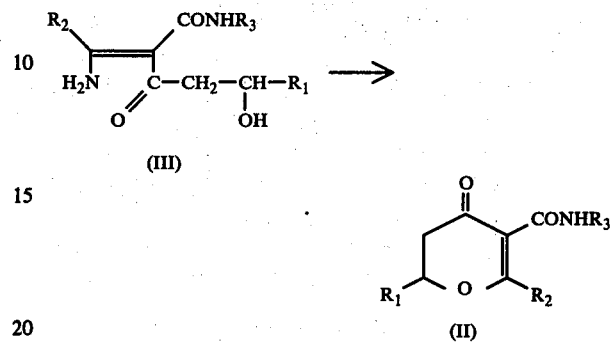

where $R_1$, $R_2$, and $R_3$ are as defined above.

The compounds of formula (II) are prepared by cyclizing a compound of the formula (III) with mineral acid in an inert solvent. The mineral acid can be concentrated or dilute hydrochloric acid, sulfuric acid, phosphoric acid, and the like, preferably concentrated hydrochloric acid. The inert solvent employed can be any solvent inert under the reaction conditions; but the lower alcohols having 1 to 4 carbon atoms, water, or mixtures thereof are preferred, especially ethyl alcohol. The temperature at which the reaction is carried out is not critical but it is preferred that the reaction be run between about 20° C. to 100° C., preferably between about 25° C. to 30° C. The time of the reaction also is not critical, but it is preferred that the reaction be run for 1 to 5 hours, especially 1.5 to 3.5 hours. The compounds of formula (II) are isolated by conventional techniques, e.g., filtration and crystallization.

The compound of formula (III) may be prepared in accordance with the following reaction scheme:

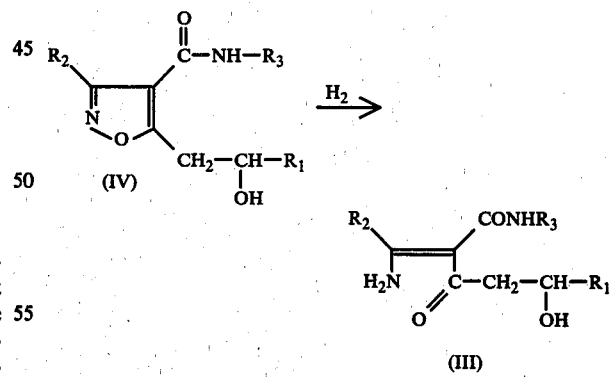

where $R_1$, $R_2$, and $R_3$ are as defined above.

The compounds of formula (III) are prepared by hydrogenating a compound of the formula (IV) with hydrogen in an inert solvent in the presence of a hydrogenation catalyst. The hydrogenation catalyst can be any of the standard hydrogenation catalysts, such as palladium on carbon, platinum oxide, Raney nickel, and the like, but 10 percent palladium on carbon is especially preferred. Although the particular inert solvent used is not critical, it is preferred that the reaction is carried out in solvents, such as the lower alkanols of 1 to 4 carbon atoms, dioxane, tetrahydrofuran, water, or mixtures of the above, especially ethanol. The temperature at which the reaction is carried out is also not critical, but it is preferred that the reaction be run between about 20° C. to 100° C., preferably between about 25° C. to 30° C., especially room temperature. The time of the reaction is not critical also, but it is preferred that the reaction be run for 1 to 18 hours, in particular, for the period of time required to absorb one equivalent of hydrogen. The compound of formula (III) is isolated by conventional techniques, e.g., filtration and evaporation.

The compounds of formula (IV) may be prepared according to the following reaction scheme:

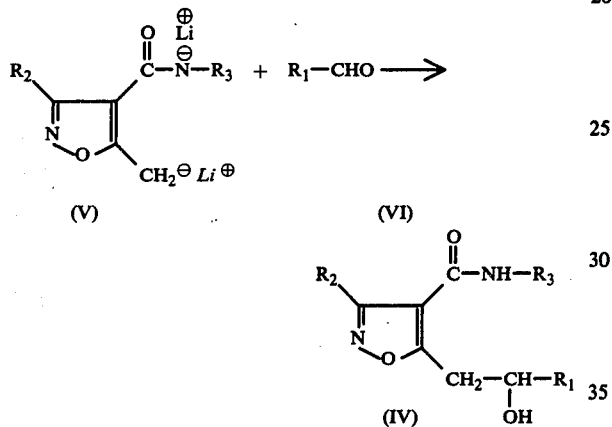

where $R_1$, $R_2$, and $R_3$ are as defined above.

The compounds of formula (IV) are prepared by treating a compound of the formula (V) with a compound of the formula (VI) in the presence of an inert organic solvent. Although the particular solvent employed is not critical, the preferred solvents include ethers, such as diethylether or tetrahydrofuran or an aliphatic hydrocarbon, such as pentane, hexane, heptane, and the like, preferably tetrahydrofuran. The temperature of the reaction is not critical, but it is preferred that the reaction be run at a temperature of from about −75° C. to −55° C., preferably from about −65° C. to −60° C. The reaction is run from about 1 to 5 hours, preferably from about 2.5 to 3.5 hours. The product is recovered using conventional techniques, e.g., trituration followed by filtration.

The compounds of formula (V) may be prepared according to the following reaction scheme:

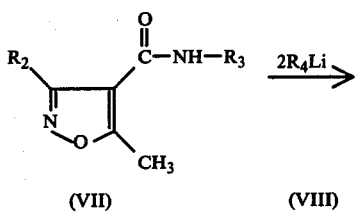

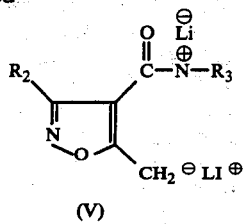

where $R_4$ is lower alkyl having 1 to 4 carbon atoms, and $R_2$ and $R_3$ are as defined above.

The compounds of formula (V) are prepared by treating a compound of the formula (VII) with a compound of the formula (VIII) in the presence of an inert organic solvent. Although the particular solvent employed is not critical, the preferred solvents include an ether such as diethylether or tetrahydrofuran or an aliphatic hydrocarbon such as pentane, hexane, heptane, and the like, preferably hexane. The temperature of the reaction is not critical, but it is preferred that the reaction be run at a temperature of from about −75° C. to −55° C., preferably from about −65° C. to −60° C. The reaction is run from about 1 to 5 hours, preferably from about 2.5 to 3.5 hours. The compound of formula (V) is not isolated but employed in situ as a starting material in the preparation of the compounds of formula (IV).

Many of the compounds of formulae (VI), (VII), and (VIII) are known and may be prepared by methods described in the literature. The compounds of formulae (VI), (VII), and (VIII) not specifically described may be prepared by analogous methods from known starting materials.

The compounds of the formula (I) are also useful in the treatment of allergic conditions, such as allergic asthma, as indicated by their histamine-release activity in the passive cutaneous anaphylaxis test in the rat. Female-rats (180–200 grams) are sensitized by intramuscular administration of 2 milligrams of egg albumin (Merck Nr. 967) dissolved in 0.1 milliliters of physiological saline and 0.5 milliliters of Haemophiluspertussis vaccine (Schweizerisches Serum and Impfinstitut, Bern; Nr. 115 325; 4 × $10^{10}$ organism/milliliter) intraperitoneally. Fourteen days later, the animals are exsanguinated, the blood centrifuged, the serum collected and deep frozen. The serum thus obtained (anti-serum) is injected intradermally (0.1 milliliters of a 1:2 diluted serum per injection site) at four sites on the backs of untreated, female rats. Twenty-four hours later, each rat is administered 32 milligrams/kilogram of the test compound, intraperitoneally or orally as a suspension in tragacanth; and either 5 or 30 minutes afterwards, in the case of intraperitoneal administration, or 60 minutes afterwards, in the case of oral administration, egg albumin (5 milligrams/kilogram i.v.) dissolved in physiological saline containing 0.25 percent Evans Blue Dye (Merck Nr. 3169) is administered. The egg albumin elicits a cutaneous anaphylactic reaction, the intensity of which is proportional to the extent to which the Evans Blue Dye diffuses into the tissue surrounding each of the four sensitization sites. Thirty minutes after the administration of the egg albumin, the rats are killed with ether, the underside of the skin of the back of each animal is exposed and the diameter of the areas of blue dye surrounding each of the four sensitization sites are measured. Each dose of the test compound is investigated in between four and six rats and the mean diameter compared with the mean value obtained in four solvent-treated control rats. The percentage inhibition is taken as the percentage of the mean diameter in the test animals relative to the mean diameter in the controls.

For the above-mentioned use as anti-allergic agents, the dosage administered will, of course, vary depending on the compound employed, mode of administration and treatment desired. However, in general, satisfactory results are obtained upon administration at a daily dosage of from about 0.1 to 50 milligrams/kilogram of animal body weight, conveniently given in divided doses two to four times daily, or in sustained release form. For the larger mammals, the total daily dosage is in the range of from about 10 to 400 milligrams, and dosage forms suitable for oral administration comprise from about 2.5 to 200 milligrams of the compound admixed with a solid or liquid pharmaceutical carrier or diluent.

Tablets and capsules containing the ingredients indicated below may be prepared by conventional techniques and are useful in the treatment of allergy at a dose of one or two tablets just before bedtime.

| Ingredients | Weight (mg.) | |
|---|---|---|
| | Tablet | Capsule |
| 2,6-diphenyl-N-methyl-4-oxo-4H-pyran-3-carboxamide | 100 | 100 |
| tragacanth | 10 | — |
| lactose | 147.5 | 200 |
| corn starch | 25 | — |
| talcum | 15 | — |
| magnesium stearate | 2.5 | — |
| Total | 300 mg. | 300 mg. |

EXAMPLE 1

3-phenyl-5-(β-hydroxyphenethyl)-N-methyl-isoxazole-4-carboxamide

A suspension of 75 grams (0.348 mole) of 3-phenyl-5,N-dimethyl-isoxazole-4-carboxamide in 1 liter of tetrahydrofuran is cooled to −65° C. and 478 milliliters of 1.6M n-butyllithium in hexane (0.765 mole) is added dropwise maintaining the temperature between −60° C. and −70° C. After the addition is complete, the orange suspension is stirred for 1½ hours at −60° C. to −70° C., and then 37.2 grams (0.350 mole) of benzaldehyde in 375 milliliters tetrahydrofuran is added dropwise maintaining the temperature between −60° C. and −70° C. After addition is complete, the mixture is stirred 1½ hours at −60° C. to −70° C. and then warmed to −30° C. and quenched by the addition of saturated ammonium chloride solution. The mixture is further diluted with tetrahydrofuran and the layers are separated. The tetrahydrofuran layer is washed twice with 50 percent brine, and once with brine, dried over anhydrous magnesium sulfate, filtered and evaporated in vacuo. The solid residue is triturated with a 50:50 mixture of ether:petroleum ether, filtered and washed with cold ether to give 3-phenyl-5-(β-hydroxyphenethyl)-N-methyl-isoxazole-4-carboxamide, m.p. 183°–184° C.

Following the above procedure and using in place of 3-phenyl-5,N-dimethyl-isoxazole-4-carboxamide, an equivalent amount of (a) 3-(p-chlorophenyl)-5,N-dimethyl-isoxazole-4-carboxamide, (b) 3-(p-fluorophenyl)-5,N-dimethyl-isoxazole-4-carboxamide, (c) 3-(p-tolyl)-5,N-dimethyl-isoxazole-4-carboxamide, (d) 3-(p-anisyl)-5,N-dimethyl-isoxazole-4-carboxamide, or (e) 3-ethyl-5,N-dimethyl-isoxazole-4-carboxamide, there is obtained (a) 3-(p-chlorophenyl)-5-(β-hydroxyphenethyl)-N-methyl-isoxazole-4-carboxamide, (b) 3-(p-fluorophenyl)-5-(β-hydroxyphenethyl)-N-methyl-isoxazole-4-carboxamide, (c) 3-(p-tolyl)-5-(β-hydroxyphenethyl)-N-methyl-isoxazole-4-carboxamide, (d) 3-(p-anisyl)-5-(β-hydroxyphenethyl)-N-methyl-isoxazole-4-carboxamide, or (e) 3-ethyl-5-(β-hydroxyphenethyl)-N-methyl-isoxazole-4-carboxamide, respectively.

Again following the same procedure and using in place of benzaldehyde an equivalent amount of (f) p-chlorobenzaldehyde, (g) p-fluorobenzaldehyde, (h) p-tolualdehyde, (i) p-anisaldehyde, or (j) pivalaldehyde, there is obtained (f) 3-phenyl-5-(4-chloro-β-hydroxyphenethyl)-N-methyl-isoxazole-4-carboxamide, (g) 3-phenyl-5-(4-fluoro-β-hydroxyphenethyl)-N-methyl-isoxazole-4-carboxamide, (h) 3-phenyl-5-(4-methyl-β-hydroxyphenethyl)-N-methyl-isoxazole-4-carboxamide, (i) 3-phenyl-5-(4-methoxy-β-hydroxyphenethyl)-N-methyl-isoxazole-4-carboxamide, or (j) 3-phenyl-5-(3,3-dimethyl-2-hydroxybutyl)-N-methyl-isoxazole-4-carboxamide, respectively.

Again following the above procedure and using in place of 3-phenyl-5,N-dimethyl-isoxazole-4-carboxamide an equivalent amount of 3-ethyl-5,N-dimethyl-isoxazole-4-carboxamide and in place of benzaldehyde an equivalent amount of pivaldehyde there is obtained (k) 3-ethyl-5-(3,3-dimethyl-2-hydroxybutyl)-N-methyl-isoxazole-4-carboxamide.

EXAMPLE 2

2-(α-aminobenzylidene)-5-hydroxy-N-methyl-3-oxo-5-phenyl valeramide

A mixture of 30.0 grams (0.093 mole) of 3-phenyl-5-(β-hydroxyphenethyl)-N-methyl-isoxazole-4-carboxamide, 600 milliliters of ethanol and 3.0 grams of 10 percent Palladium on carbon in hydrogenated at 50 p.s.i. until 1 equivalent of hydrogen is absorbed (about 5 hours). The mixture is filtered and the filtrate evaporated in vacuo. The residue is then crystallized from methylene chloride petroleum ether to give 2-(α-aminobenzylidene)-5-hydroxy-N-methyl-3-oxo-5-phenylvaleramide, m.p. 72° C.–76° C.

Following the above procedure and using in place of 3-phenyl-5-(β-hydroxyphenethyl)-N-methyl-isoxazole-4-carboxamide, an equivalent amount of (a) 3-(p-chlorophenyl)-5-(β-hydroxyphenethyl)-N-methyl-isoxazole-4-carboxamide, (b) 3-(p-fluorophenyl)-5-(β-hydroxyphenethyl)-N-methyl-isoxazole-4-carboxamide, (c) 3-(p-tolyl)-5-(β-hydroxyphenethyl)-N-methyl-isoxazole-4-carboxamide,
(d) 3-(p-anisyl)-5-(β-hydroxyphenethyl)-N-methyl-isoxazole-4-carboxamide,
(e) 3-ethyl-5-(β-hydroxyphenethyl)-N-methyl-isoxazole-4-carboxamide
(f) 3-phenyl-5-(4-chloro-β-hydroxyphenethyl)-N-methyl-isoxazole-4-carboxamide,
(g) 3-phenyl-5-(4-fluoro-β-hydroxyphenethyl)-N-methyl-isoxazole-4-carboxamide,
(h) 3-phenyl-5-(4-methyl-β-hydroxyphenethyl)-N-methyl-isoxazole-4-carboxamide,
(i) 3-phenyl-5-(4-methoxy-β-hydroxyphenethyl)-N-methyl-isoxazole-4-carboxamide,
(j) 3-phenyl-5-(3,3-dimethyl-2-hydroxybutyl-N-methyl-isoxazole-4-carboxamide, or
(k) 3-ethyl-5-(3,3-dimethyl-2-hydroxybutyl)-N-methyl-isoxazole-4-carboxamide, there is obtained
(a) 2-(α-amino-[p-chlorobenzylidene])-5-hydroxy-N-methyl-3-oxo-5-phenylvaleramide,
(b) 2-(α-amino-[p-fluorobenzylidene])-5-hydroxy-N-methyl-3-oxo-5-phenylvaleramide,
(c) 2-(α-amino-[p-methylbenzylidene])-5-hydroxy-N-methyl-3-oxo-5-phenylvaleramide,
(d) 2-(α-amino-[p-methoxybenzylidene])-5-hydroxy-N-methyl-3-oxo-5-phenylvaleramide,
(e) 2-(α-aminopropylidene)-5-hydroxy-N-methyl-3-oxo-5-phenylvaleramide,
(f) 2-(α-aminobenzylidene)-5-hydroxy-N-methyl-3-oxo-5-(p-chlorophenyl)-valeramide,
(g) 2-(α-aminobenzylidene)-5-hydroxy-N-methyl-3-oxo-5-(p-fluorophenyl)-valeramide,
(h) 2-(α-aminobenzylidene)-5-hydroxy-N-methyl-3-oxo-5-(p-tolyl)-valeramide,
(i) 2-(α-aminobenzylidene)-5-hydroxy-N-methyl-3-oxo-5-(p-anisyl) valeramide,
(j) 2-(α-aminobenzylidene)-5-hydroxy-6,6-N-trimethyl-3-oxo-heptanamide, or
(k) 2-(α-aminopropylidene)-5-hydroxy-6,6-N-trimethyl-3-oxo-heptanamide, respectively.

EXAMPLE 3

5,6-dihydro-2,6-diphenyl-N-methyl-4-oxo-4H-pyran-3-carboxamide

A solution of 21.4 grams (0.066 mole) of 2-(α-aminobenzylidene)-5-hydroxy-N-methyl-3-oxo-5-phenylvaleramide in 220 milliliters of ethanol is treated by dropwise addition with 10 milliliters of concentrated hydrochloric acid. The resulting suspension is stirred for 1.5 hours at room temperature. Ether is then added, and the mixture is filtered. The resulting solid is triturated thoroughly with hot methanol to give 5,6-dihydro-2,6-diphenyl-N-methyl-4-oxo-4H-pyran-3-carboxamide, m.p. 212° C.–214° C.

Following the above procedure, but using in place of the 2-(α-aminobenzylidene)-5-hydroxy-N-methyl-3-oxo-5-phenylvaleramide an equivalent amount of (a) 2-(α-amino-[p-chlorobenzylidene])-5-hydroxy-N-methyl-3-oxo-5-phenylvaleramide,
(b) 2-(α-amino-[p-fluorobenzylidene])-5-hydroxy-N-methyl-3-oxo-5-phenylvaleramide,
(c) 2-(α-amino-[p-methylbenzylidene])-5-hydroxy-N-methyl-3-oxo-5-phenylvaleramide,
(d) 2-(α-amino-[p-methoxybenzylidene])-5-hydroxy-N-methyl-3-oxo-5-phenylvaleramide,
(e) 2-(α-aminopropylidene])-5-hydroxy-N-methyl-3-oxo-5-phenylvaleramide,
(f) 2-(α-aminobenzylidene)-5-hydroxy-N-methyl-3-oxo-5-(p-chlorophenyl)-valeramide,
(g) 2-(α-aminobenzylidene)-5-hydroxy-N-methyl-3-oxo-5-(p-fluorophenyl)-valeramide,
(h) 2-(α-aminobenzylidene)-5-hydroxy-N-methyl-3-oxo-5-(p-tolyl)-valeramide,
(i) 2-(α-aminobenzylidene)-5-hydroxy-N-methyl-3-oxo-5-(p-anisyl)-valeramide, or
(j) 2-(α-aminobenzylidene)-5-hydroxy-6,6-N-trimethyl-3-oxo-heptanamide, or
(k) 2-(α-aminopropylidene)-5-hydroxy-6,6-N-trimethyl-3-oxo-heptanamide, there is obtained
(a) 5,6-dihydro-2-(p-chlorophenyl)-6-phenyl-N-methyl-4-oxo-4H-pyran-3-carboxamide,
(b) 5,6-dihydro-2-(p-fluorophenyl)-6-phenyl-N-methyl-4-oxo-4H-pyran-3-carboxamide,
(c) 5,6-dihydro-2-(p-tolyl)-6-phenyl-N-methyl-4-oxo-4H-pyran-3-carboxamide,
(d) 5,6-dihydro-2-(p-anisyl)-6-phenyl-N-methyl-4-oxo-4H-pyran-3-carboxamide,
(e) 5,6-dihydro-2-ethyl-6-phenyl-N-methyl-4-oxo-4H-pyran-3-carboxamide,
(f) 5,6-dihydro-2-phenyl-6-(p-chlorophenyl)-N-methyl-4-oxo-4H-pyran-3-carboxamide,
(g) 5,6-dihydro-2-phenyl-6-(p-fluorophenyl)-N-methyl-4-oxo-4H-pyran-3-carboxamide,
(h) 5,6-dihydro-2-phenyl-6-(p-tolyl)-N-methyl-4-oxo-4H-pyran-3-carboxamide,
(i) 5,6-dihydro-2-phenyl-6-(p-anisyl)-N-methyl-4-oxo-4H-pyran-3-carboxamide,
(j) 5,6-dihydro-2-phenyl-6-(t-butyl)-N-methyl-4-oxo-4H-pyran-3-carboxamide, or
(k) 5,6-dihydro-2-ethyl-6-(t-butyl)-N-methyl-4-oxo-4H-pyran-3-carboxamide, respectively.

EXAMPLE 4

2,6-diphenyl-N-methyl-4-oxo-4H-pyran-3-carboxamide

A mixture of 10.0 grams (0.0324 mole) of 5,6-dihydro-2,6-diphenyl-N-methyl-4-oxo-4H-pyran-3-carboxamide, 11.0 grams (0.0485 mole) of dichloro dicyanoquinone and 200 milliliters of benzene is refluxed for 18 hours. The mixture is cooled and the precipitate filtered and washed with benzene and methylenedichloride. The filtrate is evaporated to dryness and the residue is partitioned between methylenedichloride and 2N sodium hydroxide and the layers separated. The organic layer is washed with 2N sodium hydroxide, water and 50 percent brine, dried over magnesium sulfate, filtered and evaporated in vacuo. The residue is dissolved in a hot 50:50 mixture of ethanol:methanol, treated with decolorizing charcoal, filtered and evaporated in vacuo. The residue is crystallized from ethanol to give 2,6-diphenyl-N-methyl-4-oxo-4H-pyran-3-carboxamide, m.p. 196° C.–197° C.

When the above procedure is carried out using in place of the 5,6-dihydro-2,6-diphenyl-N-methyl-4-oxo-4H-pyran-3-carboxamide an equivalent amount of (a) 5,6-dihydro-2-(p-chlorophenyl)-6-phenyl-N-methyl-4-oxo-4H-pyran-3-carboxamide,
(b) 5,6-dihydro-2-(p-fluorophenyl)-6-phenyl-N-methyl-4-oxo-4H-pyran-3-carboxamide,
(c) 5,6-dihydro-2-(p-tolyl)-6-phenyl-N-methyl-4-oxo-4H-pyran-3-carboxamide, (d) 5,6-dihydro-2-(p-anisyl)-6-phenyl-N-methyl-4-oxo-4H-pyran-3-carboxamide,
(e) 5,6-dihydro-2-ethyl-6-phenyl-N-methyl-4-oxo-4H-pyran-3-carboxamide,
(f) 5,6-dihydro-2-phenyl-6-(p-chlorophenyl)-N-methyl-4-oxo-4H-pyran-3-carboxamide,
(g) 5,6-dihydro-2-phenyl-6-(p-fluorophenyl)-N-methyl-4-oxo-4H-pyran-3-carboxamide,
(h) 5,6-dihydro-2-phenyl-6-(p-tolyl)-N-methyl-4-oxo-4H-pyran-3-carboxamide,
(i) 5,6-dihydro-2-phenyl-6-(p-anisyl)-N-methyl-4-oxo-4H-pyran-3-carboxamide,
(j) 5,6-dihydro-2-phenyl-6-(t-butyl)-N-methyl-4-oxo-4H-pyran-3-carboxamide, or
(k) 5,6-dihydro-2-ethyl-6-(t-butyl)-N-methyl-4-oxo-4H-pyran-3-carboxamide,
there is obtained
(a) 2-(p-chlorophenyl)-6-phenyl-N-methyl-4-oxo-4H-pyran-3-carboxamide,
(b) 2-(p-fluorophenyl)-6-phenyl-N-methyl-4-oxo-4H-pyran-3-carboxamide,
(c) 2-(p-tolyl)-6-phenyl-N-methyl-4-oxo-4H-pyran-3-carboxamide,
(d) 2-(p-anisyl)-6-phenyl-N-methyl-4-oxo-4H-pyran-3-carboxamide,
(e) 2-ethyl-6-phenyl-N-methyl-4-oxo-4H-pyran-3-carboxamide,
(f) 2-phenyl-6-(p-chlorophenyl)-N-methyl-4-oxo-4H-pyran-3-carboxamide,
(g) 2-phenyl-6-(p-fluorophenyl)-N-methyl-4-oxo-4H-pyran-3-carboxamide,
(h) 2-phenyl-6-(p-tolyl)-N-methyl-4-oxo-4H-pyran-3-carboxamide,
(i) 2-phenyl-6-(p-anisyl)-N-methyl-4-oxo-4H-pyran-3-carboxamide,
(j) 2-phenyl-6-(t-butyl)-N-methyl-4-oxo-4H-pyran-3-carboxamide, or
(k) 2-ethyl-6-(t-butyl)-N-methyl-4-oxo-4H-pyran-3-carboxamide, respectively.

What is claimed is:

1. A compound of the formula:

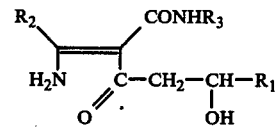

where $R_1$ and $R_2$ each independently is lower alkyl, or

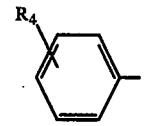

where $R_4$ is hydrogen, halogen having an atomic weight of from 19 to 36, lower alkoxy or lower alkyl,
and $R_3$ is lower alkyl.

2. The compound of claim 1, which is 2-(α-aminobenzylidene)-5-hydroxy-N-methyl-3-oxo-5-phenylvaleramide.

* * * * *

UNITED STATES PATENT AND TRADEMARK OFFICE
CERTIFICATE OF CORRECTION

PATENT NO. : 4,136,114
DATED : Jan. 23, 1979
INVENTOR(S) : Jeffrey Nadelson

It is certified that error appears in the above-identified patent and that said Letters Patent are hereby corrected as shown below:

Col. 4, lines 1-11, delete formula V and insert in its place corrected formula V

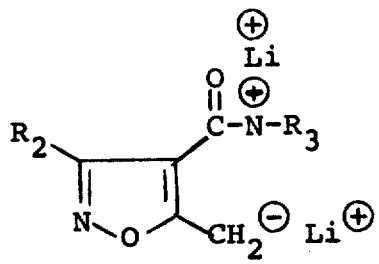

(V)

Signed and Sealed this

Thirty-first Day of July 1979

[SEAL]

Attest:

Attesting Officer

LUTRELLE F. PARKER
Acting Commissioner of Patents and Trademarks